(12) United States Patent
Bhattacharyya et al.

(10) Patent No.: US 9,266,809 B2
(45) Date of Patent: *Feb. 23, 2016

(54) PROCESS FOR PRODUCING TEREPHTHALIC ACID

(71) Applicants: UOP LLC, Des Plaines, IL (US); Boreskov Institute of Catalysis, Novosibirsk (RU)

(72) Inventors: Alakananda Bhattacharyya, Glen Ellyn, IL (US); Joseph A. Kocal, Glenview, IL (US); Joel T. Walenga, Lake Zurich, IL (US); Nikolay Y. Adonin, Novosibirsk (RU); Nina I. Kuznetsova, Novosibirsk (RU); Bair S. Bal'zhinimaev, Novosibirsk (RU)

(73) Assignees: UOP LLC, Des Plaines, IL (US); BORESKOV INSTITUTE OF CATALYSIS, Novosibirsk (RU)

( * ) Notice: Subject to any disclaimer, the term of this patent is extended or adjusted under 35 U.S.C. 154(b) by 0 days.

This patent is subject to a terminal disclaimer.

(21) Appl. No.: 14/535,375

(22) Filed: Nov. 7, 2014

(65) Prior Publication Data

US 2015/0065747 A1    Mar. 5, 2015

Related U.S. Application Data

(63) Continuation of application No. 13/155,553, filed on Jun. 8, 2011, now Pat. No. 8,884,055.

(60) Provisional application No. 61/360,228, filed on Jun. 30, 2010.

(51) Int. Cl.
*C07C 51/16* (2006.01)
*C07C 51/265* (2006.01)
*C07C 51/42* (2006.01)

(52) U.S. Cl.
CPC .............. *C07C 51/265* (2013.01); *C07C 51/42* (2013.01); *Y02P 20/542* (2015.11)

(58) Field of Classification Search
CPC ............................. C07C 51/487; C07C 63/26
USPC ...................................................... 562/412
See application file for complete search history.

(56) References Cited

U.S. PATENT DOCUMENTS 8,884,055 B2 * 11/2014 Bhattacharyya et al. ...... 562/412
2009/0326265 A1 * 12/2009 Hashmi ................. C07C 51/265
                                                 562/416

* cited by examiner

*Primary Examiner* — Porfirio Nazario Gonzalez
*Assistant Examiner* — Kofi Adzamli

(57) ABSTRACT

A solid terephthalic acid composition and a process for producing terephthalic acid from para-xylene. The process comprises forming a mixture comprising the para-xylene, a solvent, a bromine source, and a catalyst; and oxidizing the para-xylene by contacting the mixture with an oxidizing agent at oxidizing conditions to produce a solid oxidation product comprising terephthalic acid, para-toluic acid, 4-carboxybenzaldehyde. The solvent comprises a carboxylic acid having from 1 to 7 carbon atoms and an dialkyl imidazolium ionic liquid; and the catalyst comprises at least one of cobalt, titanium, manganese, chromium, copper, nickel, vanadium, iron, molybdenum, tin, cerium, and zirconium. The solid terephthalic acid composition comprises, less than about 4,000 ppm-wt 4-carboxybenzaldehyde content, and more than about 2,000 ppm-wt a para-toluic acid.

16 Claims, No Drawings

PROCESS FOR PRODUCING TEREPHTHALIC ACID

CROSS-REFERENCE TO RELATED APPLICATION

This application is a Continuation of copending U.S. application Ser. No. 13/155,553 which was filed on Jun. 8, 2011, and claimed the benefit of U.S. Provisional Application No. 61/360,228 which was filed on Jun. 30, 2010.

JOINT RESEARCH AGREEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are 1) UOP LLC and 2) Boreskov Institute of Catalysis.

FIELD OF THE INVENTION

This invention relates to solid terephthalic acid compositions and processes for producing terephthalic acid from a feed stock comprising para-xylene. More particularly, the invention relates to the oxidation of para-xylene in the presence of a solvent comprising a carboxylic acid and an ionic liquid.

BACKGROUND OF THE INVENTION

The oxidation of alkyl aromatic compounds, e.g., toluene and xylenes are important commercial process. A variety of oxidation products may be obtained including aromatic carboxylic acids such as terephthalic acid (1,4-benzenedicarboxylic acid) which is used, for example, in the polymer industry.

U.S. Pat. No. 2,833,816 discloses processes for oxidizing aromatic compounds to the corresponding aromatic carboxylic acids. A process for the liquid phase oxidation of alkyl aromatic compounds uses molecular oxygen, a metal or metal ions, and bromine or bromide ions in the presence of an acid. The metals may include cobalt and/or manganese. Exemplary acids are lower aliphatic mono carboxylic acids containing 1 to 8 carbon atoms, especially acetic acid.

U.S. Pat. No. 6,355,835 discloses a process for the preparation of benzene dicarboxylic acids by liquid phase oxidation of xylene isomers using oxygen or air by oxidising in the presence of acetic acid as solvent, cobalt salt as catalyst and an initiator. The oxidation step is followed by flashing the said reaction mixture to remove volatile substances and cooling and filtering to get crude benzene di-carboxylic acid as a solid product and filtrate. Recrystallizing the crude benzene dicarboxylic acid to obtain at least 99% purity and recycling of the filtrate are also disclosed.

U.S. Pat. No. 7,094,925 discloses a process for the oxidation of an alkyl-aromatic compound, wherein the aromatic compound is admixed with an oxidising agent or sulfur compound in the presence of an ionic liquid. Air, dioxygen, peroxide, superoxide, any other form of active oxygen, nitrite, nitrate, nitric acid or other oxides (or oxyhalides) of nitrogen (hydrate or anhydrous) are preferably used as the oxidising agent. The process is usually under Bronsted acidic conditions. The product of the oxidation reaction is preferably a carboxylic acid or ketone or an intermediate compound in the oxidation such as an aldehyde, or alcohol. The oxidation is preferably performed in an ionic liquid containing an acid promoter such as methanesulfonic acid.

US 2009/0326265 A1 discloses a process for preparing an aromatic polycarboxylic acid by liquid phase oxidation of a di- or tri-substituted benzene or naphtalene compound, the process comprising a step of contacting the aromatic compound with an oxidant in the presence of a carboxylic acid solvent, a metal catalyst and a promoter in a reaction zone, wherein the promoter is an ionic liquid comprising an organic cation and a bromide or iodide anion. Advantages of this process include high conversion without severe corrosion problems otherwise associated with halogen-containing compounds as promoter. The process does not necessitate the use of special corrosion-resistant material or liners in the process equipment; thus offering savings on investment and maintenance costs and increasing plant reliability. The process of the invention is especially suited for production of terephthalic acid from p-xylene.

It is also known in the art that the oxidation products such as aromatic aldehydes, aromatic alcohols, aromatic ketones, and aromatic carboxylic acids may solidify or crystallize at oxidation conditions and/or as the reaction mixture cools. Thus, mixtures of oxidation products may be produced which require further processing to increase the purity of the desired product. In the production of terephthalic acid, the oxidation product is often referred to as crude terephthalic acid as it contains impurities including color bodies and intermediate oxidation products especially 4-carboxybenzaldehyde (4-CBA). To obtain polymer grade or purified terephthalic acid, various purification steps are known in the art including: washing the crude terephthalic acid with water and/or a solvent, additional oxidation or crystallization steps, and reacting a solution of dissolved crude terephthalic acid with hydrogen at hydrogenation conditions usually including a catalyst comprising palladium and carbon. Often several purification steps are used.

U.S. Pat. No. 7,692,036 discloses an optimized process and apparatus for more efficiently and economically carrying out the liquid-phase oxidation of an oxidizable compound. Such liquid-phase oxidation is carried out in a bubble column reactor that provides for a highly efficient reaction at relatively low temperatures. When the oxidized compound is para-xylene and the product from the oxidation reaction is crude terephthalic acid (CTA), such CTA product can be purified and separated by more economical techniques than could be employed if the CTA were formed by a conventional high-temperature oxidation process.

There remains a need in the art for alternate processes that produce terephthalic acid. In addition, processes that produce terephthalic acid and terephthalic acid compositions that are less costly and time consuming to purify are desirable. Terephthalic acid compositions having different ratios of contaminants may provide new intermediates useful as raw materials in other applications.

SUMMARY OF THE INVENTION

The invention provides new terephthalic acid compositions. In another aspect, the invention is a process for the oxidation of para-xylene to terephthalic acid. It has been discovered that the invention may be used to produce solid terephthalic acid compositions having different amounts of contaminants relative to those observed in conventional processes. In an embodiment, the invention provides terephthalic acid compositions that are less costly to purify. In another embodiment, the invention produces polymer grade or purified terephthalic acid without the use of catalytic hydrogenation.

In an embodiment, the invention is a process for producing terephthalic acid from para-xylene, the process comprising forming a mixture comprising the para-xylene, a solvent, a bromine source, and a catalyst; and oxidizing the para-xylene by contacting the mixture with an oxidizing agent at oxidizing conditions to produce a solid oxidation product comprising terephthalic acid, 4-carboxybenzaldehyde, and para-toluic acid. The solvent comprises a carboxylic acid having from 1 to 7 carbon atoms and an dialkyl imidazolium ionic liquid; and the catalyst comprises at least one of cobalt, titanium, manganese, chromium, copper, nickel, vanadium, iron, molybdenum, tin, cerium, and zirconium.

In another aspect, the invention is a solid terephthalic acid composition comprising terephthalic acid, para-toluic acid, and 4-carboxybenzaldehyde; wherein the composition has a 4-carboxybenzaldehyde content of less than about 4,000 ppm-wt, and a para-toluic acid content of more than about 2,000 ppm-wt. In an embodiment, the solid terephthalic acid composition has a 4-carboxybenzaldehyde content of less than about 100 ppm-wt, and a para-toluic acid content of more than about 2,000 ppm-wt.

DETAILED DESCRIPTION OF THE INVENTION

In general, the invention relates to terephthalic acid compositions and processes for the oxidation of para-xylene to terephthalic acid. In broad terms, the invention is a process for producing terephthalic acid from para-xylene comprising forming a mixture comprising the para-xylene, a solvent, a bromine source, and a catalyst; and oxidizing the para-xylene by contacting the mixture with an oxidizing agent at oxidizing conditions to produce a solid oxidation product comprising terephthalic acid, 4-carboxybenzaldehyde, and para-toluic acid.

Para-xylene may be supplied to the process as a pure feed stream or the feed stream may also include other compounds. In an embodiment, the feed stream has a para-xylene content of at least 98 wt %. In another embodiment the feed stream has a para-xylene content of at least 99 wt %. As the oxidation reaction generally proceeds through successive degrees of oxidization, suitable feed compounds also include partially oxidized para-xylene compounds. Examples include para-toluic acid, 4-carboxybenzaldehyde (4-CBA), terephthalic aldehyde, para-toluic alcohol, para-tolualdehyde, and 4-carboxybenzylalcohol. In an embodiment, at least 98 wt % of the feed stream is para-xylene and partially oxidized para-xylene compounds.

In addition to para-xylene, the mixture comprises a solvent, a bromine source, and a catalyst. The solvent comprises a carboxylic acid having from 1 to 7 carbon atoms and an ionic liquid. In an embodiment, the carboxylic acid comprises acetic acid. The solvent may contain more than one carboxylic acid. For example the solvent may further comprise benzoic acid. In another embodiment, the carboxylic acid of the solvent is acetic acid.

The solvent also comprises an ionic liquid. Relative to conventional processes the amount of the carboxylic acid solvent is decreased when ionic liquids are used to avoid excessive solvent volumes. Generally, ionic liquids are non-aqueous, organic salts composed of ions where the positive ion is charge balanced with negative ion. These materials have low melting points, often below 100° C., undetectable vapor pressure and good chemical and thermal stability. The cationic charge of the salt is localized over hetero atoms, such as nitrogen, phosphorous, sulfur, arsenic, boron, antimony, and aluminum, and the anions may be any inorganic, organic, or organometallic species.

Ionic liquids suitable for use in the instant invention include dialkyl imidazolium ionic liquids. More than one ionic liquid may be used and additional ionic liquids may, but are not required to be dialkyl imidazolium ionic liquids. Dialkyl imidazolium ionic liquids have a cation comprising two alkyl groups extending from a five member ring of three carbon and two nitrogen atoms. In an embodiment, the alkyl groups contain from one to eight carbon atoms. There is no need for the two alkyl groups to be the same or have the same number of carbon atoms. In an embodiment, the ionic liquid cation is selected from the group consisting of 1-butyl 3-methyl imidazolium, 1-hexyl 3-methyl imidazolium, and combinations thereof.

In another embodiment, the ionic liquid comprises an anion selected from the group consisting of halides, acetate, and combinations thereof The ionic liquid may be selected from the group consisting of 1-butyl 3-methyl imidazolium acetate, 1-butyl 3-methyl imidazolium bromide, 1-hexyl 3-methyl imidazolium acetate, 1-hexyl 3-methyl imidazolium bromide, and combinations thereof In an embodiment, the ionic liquid is one of 1-butyl 3-methyl imidazolium acetate, 1-butyl 3-methyl imidazolium bromide, 1-hexyl 3-methyl imidazolium acetate, and 1-hexyl 3-methyl imidazolium bromide. In another embodiment, the ionic liquid comprises at least one of 1-butyl-3-methylimidazolium bromide and 1-butyl-3-methylimidazolium acetate. In a further embodiment, the ionic liquid comprises at least one of 1-hexyl 3-methyl imidazolium acetate and 1-hexyl 3-methyl imidazolium bromide.

In an embodiment, the solvent has a ratio of ionic liquid to carboxylic acid ranging from about 1:10 to about 10:1 by weight. In another embodiment the ratio of ionic liquid to carboxylic acid ranges from about 3:10 to about 10:1 by weight. The ratio of ionic liquid to carboxylic acid may range from about 5:10 to about 10:1 by weight. Optionally, the solvent may further comprise water. The water may be added to the mixture or generated in the mixture during the oxidation process. In an embodiment, the amount of water ranges from about 0.01 wt % to about 5 wt %, relative to the weight of the carboxylic acid having from 1 to 7 carbon atoms. The amount of water may range from about 0.1 wt % to about 2 wt %, relative to the weight of the carboxylic acid having from 1 to 7 carbon atoms. In an embodiment, the ratio of solvent to para-xylene in the mixture ranges from about 1.5:1 to about 6:1 by weight. The ratio of solvent to para-xylene may range from about 2:1 to about 4:1 by weight.

The catalyst comprises at least one of cobalt, manganese, titanium, chromium, copper, nickel, vanadium, iron, molybdenum, tin, cerium and zirconium. In an embodiment, the catalyst comprises cobalt and manganese. The metal may be in the form of an inorganic or organic salt. For example, the metal catalyst may be in the form of a carboxylic acid salt, such as, a metal acetate and hydrates thereof Exemplary catalysts include cobalt (II) acetate tetrahydrate and manganese (II) acetate, individually or in combination. In an embodiment, the amount of manganese (II) acetate is less than the amount of cobalt (II) acetate tetrahydrate by weight.

The amount of catalyst used in the invention may vary widely. For example, the amount of cobalt may range from about 0.001 wt % to about 2 wt % relative to the weight of the solvent. In an embodiment, the amount of cobalt ranges from about 0.05 wt % to about 2 wt % relative to the weight of the solvent. The amount of manganese may range from about 0.001 wt % to about 2 wt % relative to the weight of the solvent. In an embodiment, the amount of manganese ranges from about 0.05 wt % to about 2 wt % relative to the weight of the solvent. In another embodiment, the ratio of cobalt to manganese ranges from about 3:1 to about 1:2 by weight on an elemental metal basis.

Bromine sources are generally recognized in the art as being catalyst promoters and include bromine, ionic bromine, e.g. HBr, NaBr, KBr, $NH_4Br$; and/or organic bromides which are known to provide bromide ions at the oxidation conditions, such as, benzylbromide, mono- and di-bromoacetic acid, bromoacetyl bromide, tetrabromoethane, ethylene dibromide. In an embodiment, the bromine source comprises or consists essentially of or consists of hydrogen bromide. The amount of hydrogen bromide may range from about 0.01 wt % to about 5 wt %, relative to the weight of the solvent. In another embodiment, the amount of hydrogen bromide ranges from about 0.05 wt % to about 2 wt %, relative to the weight of the solvent.

Optionally, the mixture may further comprise ammonium acetate. In an embodiment, the amount of ammonium acetate ranges from about 5 wt % to about 25 wt %, relative to the weight of the solvent. The amount of ammonium acetate may range from about 10 wt % to about 20 wt %, relative to the weight of the solvent.

In an embodiment, the mixture comprises para-xylene, a solvent comprising acetic acid, a dialkyl imidazolium ionic liquid, and optionally water, a bromine source comprising hydrogen bromide, a catalyst comprising cobalt and manganese, and optionally ammonium acetate. In another embodiment, the mixture comprises para-xylene, a solvent comprising acetic acid, a dialkyl imidazolium ionic liquid comprising 1-butyl 3-methyl imidazolium acetate, and optionally water, a bromine source comprising hydrogen bromide, a catalyst comprising cobalt and manganese, and optionally ammonium acetate. In further embodiment, the mixture comprises para-xylene, a solvent comprising acetic acid, a dialkyl imidazolium ionic liquid comprising 1-butyl 3-methyl imidazolium bromide, and optionally water, a bromine source comprising hydrogen bromide, a catalyst comprising cobalt and manganese, and optionally ammonium acetate. In an embodiment, the mixture comprises para-xylene, a solvent comprising acetic acid, a dialkyl imidazolium ionic liquid comprising 1-hexyl 3-methyl imidazolium bromide, and optionally water, a bromine source comprising hydrogen bromide, a catalyst comprising cobalt and manganese, and optionally ammonium acetate. In another embodiment, the mixture comprises para-xylene, a solvent comprising acetic acid, a dialkyl imidazolium ionic liquid comprising 1-hexyl 3-methyl imidazolium acetate, and optionally water, a bromine source comprising hydrogen bromide, a catalyst comprising cobalt and manganese, and optionally ammonium acetate.

Oxidation processes according to the invention may be practiced in laboratory scale experiments through full scale commercial operations. The process may be operated in batch, continuous, or semi-continuous mode. The mixture described above may be formed in various ways. The order of addition of the mixture components (e.g. para-xylene, solvent, bromine source, and catalyst) is not critical. In an embodiment, two or more components may be combined or mixed before being combined or mixed with other components. At least a portion of the mixture provides a liquid phase, though dissolution of one or more of the mixture components may not be complete at any or some time during the process. The liquid phase may be formed by mixing the components at ambient conditions. In another embodiment, the liquid phase is formed as the temperature of the mixture increases to the oxidation temperature. The mixture may be formed prior to the oxidation step, in the same or different vessel as that used in the oxidation step. In another embodiment, the mixture is formed in an oxidation reactor, e.g. adding various streams of the components individually and/or in combination to a continuous or semi-continuous oxidation reactor. The mixture, and/or various streams of the mixture components may be heated before they are mixed together.

Though many conventional alkyl aromatic oxidation processes are typically conducted in a mixed phase, and often include three phases (e.g. solid, gas, and liquid), they are frequently referred to in the art as "liquid phase" oxidation processes because the oxidation conditions are maintained to provide at least a portion of the mixture in the liquid phase. It is also known in the art that the number of phases present may vary over time during the process. Processes according to the instant invention may also be conducted in a liquid phase or mixed phase in a similar manner as known in the art.

Conventional, liquid phase oxidation reactors as known in the art may be used to practice the invention. Examples include vessels, which may have one or more mechanical agitators, and various bubble column reactors such as those described in U.S. Pat. No. 7,692,036. It is also known to design, operate, and control such reactors and the oxidation reaction for the oxidation conditions employed including, e.g., the temperature, pressure, liquid and gas volumes, and corrosive nature of the liquid and gas phases where applicable. See, e.g. U.S. Pat. No. 7,692,036 and U.S. Pat. No. 6,137,001.

The process of the invention also comprises at least one oxidizing step wherein the para-xylene is oxidized by contacting the mixture with an oxidizing agent at oxidizing conditions to produce a solid oxidation product comprising terephthalic acid, para-toluic acid, and 4-carboxybenzaldehyde (4-CBA). The solid oxidation product may further comprise at least one of benzoic acid, terephthalic aldehyde, para-toluic alcohol, para-tolualdehyde, and 4-carboxybenzylalcohol. In another embodiment the contacting step also produces a mother liquor comprising the solvent, the bromine source, and the catalyst.

Suitable oxidizing agents for the process provide a source of oxygen atoms to oxidize the para-xylene and partially oxidized para-xylene compounds at the oxidation conditions employed. Examples of oxidizing agents include peroxides, superoxides, and nitrogen compounds containing oxygen such as nitric acids. In an embodiment, the oxidizing agent is a gas comprising oxygen, e.g. air, carbon dioxide, and molecular oxygen. The gas may be a mixture of gasses. The amount of oxygen used in the process is preferably in excess of the stoichiometric amount required for the desired oxidation reaction. In an embodiment, the amount of oxygen contacted with the mixture ranges from about 1.2 times the stoichiometric amount to about 100 times the stoichiometric amount on a molar basis. Optionally, the amount of oxygen contacted with the liquid phase mixture may range from about 2 times the stoichiometric amount to about 30 times the stoichiometric amount.

Oxidizing conditions generally include a temperature ranging from about 125° C. to about 275° C. and a pressure ranging from about atmospheric, i.e. 0 MPa(g), to about 6 MPa(g) and a residence time ranging from about 5 seconds to about 2 weeks. That is, the mixture has a temperature and a pressure within these ranges and may be maintained within these ranges for a period of time within the residence time range. In another embodiment, the temperature ranges from about 175° C. to about 225° C.; and the temperature may range from about 190° C. to about 235° C. In an embodiment, the pressure ranges from about 1.2 MPa(g) to about 6.0 MPa (g); and the pressure may range from about 1.5 MPa(g) to about 6.0 MPa(g). In a further embodiment, the residence time ranges from about 10 minutes to about 12 hours. The oxidation temperature, pressure and residence time may vary based on a variety of factors including for example, the reactor configuration, size, and whether the process is, batch, continuous, or semi-continuous. An oxidation condition may also vary based on other oxidation conditions. For example, use of a particular temperature range may enable use of a different residence time range.

In an embodiment, the oxidation product produced by the instant invention may precipitate, crystallize, or solidify in a liquid phase mixture at the oxidation conditions and/or as the mixture cools. Other compounds, including color bodies, and other oxidation products may solidify with or be trapped in the solid oxidation product thus reducing the purity of the desired product. In an embodiment, the mixture comprises a liquid phase. The mixture may comprise a gas phase such as when the oxidizing agent is added as a gas. The mixture may comprise a solid phase e.g. a mixture component, an oxidation product, or a by-product fails to dissolve or solidifies in the mixture. In an embodiment, the mixture comprises a liquid phase, a solid phase and optionally a gas phase. In another embodiment, the mixture comprises a liquid phase and a gas phase.

As noted above and discussed below, it has been discovered that the invention may be used to produce a solid oxidation product having different amounts of contaminants relative to those observed in conventional processes. In addition, the invention provides new ways to control the level of various contaminants in the solid oxidation product. In an embodiment, a process according to the invention further comprises forming the oxidation product as a solid, optionally at the oxidizing conditions, to produce the solid oxidation product and a mother liquor. The solid oxidation product may be separated from the mother liquor, i.e. the liquid phase, and the mother liquor of the process may be recycled and reused in the contacting step or other steps of the process described below.

Processes according to the invention, may comprise additional oxidizing steps. In an embodiment a second oxidation step includes a second oxidizing temperature that is lower than the temperature of the first oxidizing step. Processes according to the invention may include additional oxidizing steps of the invention as described herein, and/or the invention may be combined with other oxidizing steps such as conventional oxidizing steps known in the art. Multiple oxidation steps may be conducted in series and/or parallel and may be combined with other process steps such as purification steps described herein.

In a sequential embodiment, the invention includes a second oxidation step wherein a portion or all of the solid oxidation product, or the mother liquor, or both the solid oxidation product and the mother liquor produced in the first oxidation step forms a second mixture with a second solvent, a second bromine source, and a second catalyst. The second mixture is contacted with a second oxidizing agent at second oxidizing conditions to produce a second solid oxidation product comprising terephthalic acid, 4-carboxybenzaldehyde, and para-toluic acid. The second solvent comprises a carboxylic acid having from 1 to 7 carbon atoms and a dialkyl imidazolium ionic liquid; and the second catalyst comprises at least one of cobalt, titanium, manganese, chromium, copper, nickel, vanadium, iron, molybdenum, tin, cerium, and zirconium. The second solvent, second bromine source, second catalyst, and second oxidation conditions may individually or collectively be the same or different from those of the first oxidation step. Optionally, a portion of the para-xylene may be included in the second mixture. The optional elements and optional steps described for the first oxidation step above are equally applicable to this second oxidation step.

In a parallel embodiment, the invention further comprises a second oxidation step wherein a second mixture comprising a portion of the para-xylene, a second solvent, a second bromine source, and a second catalyst is formed. The second mixture is contacted with a second oxidizing agent at second oxidizing conditions to produce a second solid oxidation product comprising terephthalic acid, 4-carboxybenzaldehyde, and para-toluic acid. The second solvent comprises a carboxylic acid having from 1 to 7 carbon atoms and the second catalyst comprises at least one of cobalt, titanium, manganese, chromium, copper, nickel, vanadium, iron, molybdenum, tin, cerium, and zirconium. Optionally, the second solvent further comprises a dialkyl imidazolium ionic liquid. The second solvent, second bromine source, second catalyst, and second oxidation conditions may individually or collectively be the same or different from those of the first oxidation step. The optional elements and optional steps described for the first oxidation step above are equally applicable to this second oxidation step.

In another embodiment, the invention further comprises purifying the solid oxidation product comprising terephthalic acid, 4-carboxybenzaldehyde, and para-toluic acid, that is, a solid terephthalic composition. Purifying may comprise one or more additional steps to isolate and purify the solid oxidation product. Examples of purifying steps include: separating wherein a solid terephthalic composition is separated from the mother liquor or another liquid phase such as by filtration and/or centrifugation; washing wherein a solid terephthalic composition is washed, for example with water and/or another solvent component; drying a solid terephthalic composition; and hydrogenation processes. Such additional processing steps have been described in the general literature and are well known to those of ordinary skill in the art to be used in various combinations to purify solid terephthalic acid compositions. See for example, the references cited in this application and the art cited therein.

A purification step of instant invention may further comprise a one or more solvent contacting steps. A solvent contacting step comprises contacting a solid terephthalic composition such as a washed solid oxidation product with a second solvent comprising at least one of water, a carboxylic acid having from 1 to 7 carbon atoms, a dialkyl imidazolium ionic liquid, and a mother liquor to produce a second solid terephthalic composition. Solvent contacting may leach impurities from the solid terephthalic composition, and/or the solid terephthalic composition may be partially or completely dissolved in the solvent. Solvent contacting conditions include a solvent contacting temperature. The solvent contacting temperature may be lower than the oxidation temperature. In an embodiment, the solvent contacting temperature is at least 20° C. lower than the oxidizing temperature. Solvent contacting may be practiced for example in the one or more crystallizers that follow the oxidation reactor in some conventional processes. The second terephthalic composition may solidify, precipitate, or crystallize in the second solvent of the solvent contacting step. The second terephthalic composition has a higher terephthalic acid content relative to the terephthalic acid content of the solid terephthalic composition introduced to the solvent contacting step as at least some impurities have been reduced.

The terephthalic composition of the solid oxidation product made by the instant invention may be purified by known methods including the use of a hydrogenation step. In an exemplary embodiment, the solid oxidation product has a 4-carboxybenzaldehyde content low enough so that a hydrogenation step is not required. That is, the invention enables production of polymer grade or purified terephthalic acid without the need for a hydrogen step and the subsequent processing steps known in the art. In an embodiment, a process according to the invention includes one or more purification steps that exclude hydrogenation steps. That is, the purifying process steps are selected from the group of process steps consisting of washing, separating, drying, solvent contacting, and combinations thereof In an embodiment, purifying the solid oxidation product comprises separating the solid oxidation product from the mother liquor and washing the solid oxidation product. The washed solid oxidation product is contacted with a second solvent at solvent contacting conditions including a solvent contacting temperature to produce a solid terephthalic acid composition. The second solvent is selected from the group consisting of the oxidation step mother liquor, a carboxylic acid having from 1 to 7 carbon atoms, a dialkyl imidazolium ionic liquid, water, and combinations thereof In an embodiment, the solvent contacting step further produces a second mother liquor. Optionally, the solid oxidation product is at least partially dissolved in the second solvent. In an embodiment, the solvent contacting step further comprises forming the solid terephthalic acid composition at the solvent contacting conditions. Optionally, the invention further comprises separating the solid terephthalic acid composition from the second mother liquor. The process may further comprise: washing the separated, solid terephthalic acid composition with water to produced a washed solid terephthalic acid composition; and drying the washed solid terephthalic acid composition to produce a dried solid terephthalic acid composition.

In an embodiment, the second solvent is the oxidation step mother liquor. In another embodiment the second solvent is the oxidation step mother liquor and the solvent contacting temperature is lower than the oxidation temperature.

Solid oxidation products produced by processes according to the invention may have different composition than terephthalic acid compositions produced by conventional processes. Without wishing to be bound by theory, it is postulated that the use of ionic liquids according to the invention alters the solubility of terephthalic acid and/or at least some of the partially oxidized para-xylene intermediates thus altering the relative amounts of partially oxidized para-xylene intermediates which co-precipitate or co-solidify with the terephthalic acid. Thus, the invention enables simpler and less costly purification step(s) relative to conventional processes.

In another embodiment, the invention is a first solid terephthalic acid composition comprising terephthalic acid, para-toluic acid, and 4-carboxybenzaldehyde; wherein the composition has a 4-carboxybenzaldehyde content of less than about 4,000 ppm-wt and a para-toluic acid content of more than about 2,000 ppm-wt In an embodiment, the first solid terephthalic acid composition has a terephthalic acid content of at least about 80 wt %; the terephthalic acid content of the composition may be at least about 85 wt %, optionally at least about 95 wt %.

In an embodiment, the para-toluic acid content of the first solid terephthalic acid composition is more than about 4,000 ppm-wt. In another embodiment, the para-toluic acid content of the first solid terephthalic acid composition is more than about 10,000 ppm-wt. In a further embodiment, the para-toluic acid content of the first solid terephthalic acid composition is more than about 70,000 ppm-wt. Optionally, the para-toluic acid content of the first solid terephthalic acid composition ranges from about 2,000 ppm-wt to about 14 wt %. The para-toluic acid content of the first solid terephthalic acid composition may be at least 15 times greater than the 4-carboxybenzaldehyde content of the first solid terephthalic acid composition on a weight basis.

In another embodiment, the invention is a second solid terephthalic acid composition wherein the 4-carboxybenzaldehyde content of the first solid terephthalic acid composition is less than about 3,000 ppm-wt. In an embodiment, the para-toluic acid content of the second solid terephthalic acid composition is more than about 4,000 ppm-wt. In another embodiment, the para-toluic acid content of the second solid terephthalic acid composition is more than about 10,000 ppm-wt. In a further embodiment, the para-toluic acid content of the second solid terephthalic acid composition is more than about 30,000 ppm-wt. Optionally, the para-toluic acid content of the second solid terephthalic acid composition ranges from about 2,000 ppm-wt to about 9 wt %. The para-toluic acid content of the second solid terephthalic acid composition may be at least 15 times greater than the 4-carboxybenzaldehyde content of the second solid terephthalic acid composition on a weight basis.

In another embodiment, the invention is a third solid terephthalic acid composition wherein the 4-carboxybenzaldehyde content of the first solid terephthalic acid composition is less than about 1,000 ppm-wt. In an embodiment, the para-toluic acid content of the third solid terephthalic acid composition is more than about 4,000 ppm-wt. In another embodiment, the para-toluic acid content of the third solid terephthalic acid composition is more than about 8,000 ppm-wt. In a further embodiment, the para-toluic acid content of the third solid terephthalic acid composition is more than about 15,000 ppm-wt. Optionally, the para-toluic acid content of the third solid terephthalic acid composition ranges from about 2,000 ppm-wt to about 3 wt %. The para-toluic acid content of the third solid terephthalic acid composition may be at least 20 times greater than the 4-carboxybenzaldehyde content of the third solid terephthalic acid composition on a weight basis.

In another embodiment, the invention is a fourth solid terephthalic acid composition wherein the 4-carboxybenzaldehyde content of the first solid terephthalic acid composition is less than about 400 ppm-wt.

In another embodiment, the invention is a fifth solid terephthalic acid composition wherein the 4-carboxybenzaldehyde content of the first solid terephthalic acid composition is less than about 100 ppm-wt. In an embodiment, the para-toluic acid content of the fifth solid terephthalic acid composition is more than about 4,000 ppm-wt. Optionally, the para-toluic acid content of the fifth solid terephthalic acid composition ranges from about 2,000 ppm-wt to about 2 wt %. The para-toluic acid content of the fifth solid terephthalic acid composition may be at least 50 times greater than the 4-carboxybenzaldehyde content of the fifth solid terephthalic acid composition on a weight basis.

EXAMPLES

The examples are presented to further illustrate some aspects and benefits of the invention and are not to be considered as limiting the scope of the invention.

Example 1

Experimental procedure: In a fume hood, load a Parr reactor with the specified amounts of components for the given experiment seal the reactor. The Parr reactor includes a gas distributor to disperse the gas through a 1.6 mm opening into the liquid, a mechanical gas entrainment stirrer, and baffles to ensure thorough mixing. Install the Parr reactor in a heater assembly at room temperature and connect a gas supply line to the reactor and a condenser to the reactor outlet. During operation, gases exit the reactor through the condenser then a trap, then a back-pressure regulator. Connect a safety vent having a rupture disk, and thermocouples to the reactor. Connect a cooling water recirculator to the condenser and begin to recirculate cooling water. Pressure test the Parr reactor at room temperature and 1.4 MPa(g) (200 psig) using nitrogen until there is no decrease in pressure for 15 minutes. Set the back pressure regulator on the reactor outlet to the experimental pressure and pressure test the reactor under nitrogen. Begin raising the reactor temperature to the experimental temperature under the nitrogen atmosphere. Always follow all instructions for the specific reactor including temperature and pressure limits. When the reactor reaches the desired temperature begin adding air at the experimental rate and monitor the reactor temperature and pressure for the duration of the test. During the test, the air flow into the reactor is maintained at 1250 or 2500 standard $cm^3$ per minute, the pressure is maintained at 4.1 MPa(g), and the stirrer is maintained at 1600 rpm. At the end of the test shut off the heater, cut the air flow and allow the reactor to cool. When the reactor cools to less than about 35° C., open the back pressure valve, stop the cooling water, and remove and empty the reactor to obtain the solid oxidation product and mother liquor.

The mother liquor and products are filtered under vacuum to separate the solids and liquid. The solids are then mixed with approximately 100 cc deionized water at room temperature and decanted. The room temperature deionized water mixing and decanting is repeated two additional times. A fourth wash with deionized water is heated to approximately 95° C. for 30 minutes and then filtered. The solids are dried at 80° C. for 8-24 hours before analyzing.

Examples 2-9

Examples 2-9 were individual tests conducted using the equipment and procedure given in Example 1. The components of the mixture, given in grams, operating temperature, time, and air flow, and results are given in Table 1.

Example 2 (Comparative)

Conventional test run without ionic liquids to demonstrate the level of impurities made using conventional solvents under standard oxidizing conditions.

Example 3

Same oxidizing conditions as Example 2 except ionic liquids were substituted for some of the acetic acid. Incorporating ionic liquids significantly reduces the 4-CBA impurity, but causes higher levels of p-toluic acid and benzoic acid.

Example 4

Repeat of Example 3 except the oxidizing temperature was increased from 200 to 215° C. Increasing the temperature significantly reduced the 4-CBA and p-toluic acid content compared to Example 3, but caused an increase in benzoic acid.

Example 5

Same oxidizing conditions as Example 3. 1-butyl-3-methylimidazolium acetate was not used and the amounts of acetic acid, ammonium acetate and 1-butyl-3-methylimidazolium bromide were increased. Here, both the 4-CBA and p-toluic acid are significantly reduced compared to the conventional test (Example 2). The benzoic acid level is still higher than Example 2, but lower than Example 3.

Example 6

Repeat of Example 3 except the oxidation time was reduced to 6 hours, which resulted in higher 4-CBA and p-toluic acid impurities, and less benzoic acid.

Example 7

Repeat of Example 6 except ammonium acetate was not used. Using ammonium acetate significantly reduces the 4-CBA but results in higher p-toluic acid.

Example 8

Modified mixture components, increase air flow to 2500 standard $cm^3$ per minute, increased oxidation temperature to 215° C. and decreased oxidation time to 3 hours. Changes significantly reduce the 4-CBA.

Example 9

Repeat of Example 8 except tetrabutylphosphonium bromide was used instead of 1-butyl-3-methylimidazolium bromide and 1-butyl-3-methylimidazolium acetate and ammonium acetate were not used.

TABLE 1

| Example Number | 2 | 3 | 4 | 5 | 6 | 7 | 8 | 9 |
|---|---|---|---|---|---|---|---|---|
| Oxidation Temperature, ° C. | 200 | 200 | 215 | 200 | 200 | 200 | 215 | 215 |
| Oxidation Time, hours | 10 | 10 | 10 | 10 | 6 | 6 | 3 | 3 |
| Air Flow, standard $cm^3$ per minute | 1250 | 1250 | 1250 | 1250 | 1250 | 1250 | 2500 | 2500 |
| Mixture Components, grams | | | | | | | | |
| para-xylene | 20.0 | 20.0 | 20.0 | 20.0 | 20.0 | 20.0 | 20.0 | 20.0 |
| glacial acetic acid | 100.0 | 44.0 | 44.0 | 60.0 | 44.0 | 44.0 | 50.0 | 80.0 |
| water | 2 | 0.4 | 0.4 | 0.4 | 0.4 | 0.4 | 0.4 | 0.4 |
| 1-butyl-3-methylimidazolium acetate | 0 | 20.0 | 20.0 | 0 | 20.0 | 20.0 | 10.0 | 0 |
| 1-butyl-3-methylimidazolium bromide | 0 | 16.0 | 16.0 | 20.0 | 16.0 | 16.0 | 20.0 | 0 |
| tetrabutylphosphonium bromide | 0 | 0 | 0 | 0 | 0 | 0 | 0 | 20.0 |
| ammonium acetate | 0 | 12.0 | 12.0 | 20.0 | 12.0 | 0.0 | 20.0 | 0 |
| hydrogen bromide | 0.4 | 0.4 | 0.4 | 0.4 | 0.4 | 0.4 | 0.4 | 0.4 |
| cobalt (II) acetate tetrahydrate | 0.8 | 0.8 | 0.8 | 0.8 | 0.8 | 0.8 | 0.8 | 0.8 |
| manganese (II) acetate | 0.6 | 0.6 | 0.6 | 0.6 | 0.6 | 0.6 | 0.6 | 0.6 |

TABLE 1-continued

| Example Number | 2 | 3 | 4 | 5 | 6 | 7 | 8 | 9 |
|---|---|---|---|---|---|---|---|---|
| Analysis of solid product | | | | | | | | |
| terephthalic acid, wt % | 98.5 | 97.8 | 98.9 | 99.9 | 96.4 | 97.0 | 99.9 | 98.4 |
| para-toluic acid, ppm-wt | 2,340 | 19,600 | 620 | 412 | 33,364 | 13,964 | 727 | 1,753 |
| 4-carboxybenzaldehyde, ppm-wt | 12,493 | 424 | 87 | 316 | 1,480 | 15,476 | 76 | 13,418 |
| benzoic acid, ppm-wt | 167 | 1,742 | 5,001 | 421 | 532 | 430 | 640 | 79 |
| 4-hydoxymethylbenzoic acid, ppm-wt | 403 | 678 | 0 | 0 | 989 | 496 | 0 | 253 |

The invention claimed is:

1. A process for producing terephthalic acid from para-xylene, the process comprising:

forming a mixture comprising the para-xylene, a solvent, a bromine source, a catalyst and optionally ammonium acetate; and oxidizing the para-xylene by contacting the mixture with an oxidizing agent at oxidizing conditions to produce a solid oxidation product, the solid oxidation product comprising terephthalic acid, 4-carboxybenzaldehyde, and para-toluic acid;

wherein the solvent comprises a carboxylic acid having from 1 to 7 carbon atoms, a dialkyl imidazolium ionic liquid, and optionally water; and the catalyst comprises at least one of cobalt, titanium, manganese, chromium, copper, nickel, vanadium, iron, molybdenum, tin, cerium, and zirconium.

2. The process of claim 1 wherein the carboxylic acid comprises acetic acid.

3. The process of claim 1 wherein the oxidizing agent is a gas comprising oxygen.

4. The process of claim 1 wherein the solvent has a ratio of ionic liquid to carboxylic acid ranging from about 1:10 to about 10:1 by weight.

5. The process of claim 1 wherein the oxidizing conditions comprise a pressure ranging from about 0 MPa(g) to about 6 MPa(g).

6. The process of claim 1 wherein the oxidizing conditions comprise a temperature ranging from about 125° C. to about 275° C.

7. The process of claim 1 wherein a ratio of the solvent to the para-xylene ranges from about 1.5:1 to about 6:1 by weight.

8. The process of claim 1 wherein an anion of the ionic liquid is selected from the group consisting of halides, acetate, and combinations thereof.

9. The process of claim 8 wherein the ionic liquid cation is selected from the group consisting of 1-butyl 3-methyl imidazolium, 1-hexyl 3-methyl imidazolium, and combinations thereof.

10. The process of claim 9 wherein the ionic liquid is selected from the group consisting of 1-butyl 3-methyl imidazolium acetate, 1-butyl 3-methyl imidazolium bromide, 1-hexyl 3-methyl imidazolium acetate, 1-hexyl 3-methyl imidazolium bromide, and combinations thereof.

11. The process of claim 1 wherein the catalyst comprises cobalt and manganese.

12. The process of claim 1 wherein the bromine source is at least one of HBr, NaBr, KBr, NH4Br, benzylbromide, monobromoacetic acid, di-bromoacetic acid, bromoacetyl bromide, tetrabromoethane, and ethylene di-bromide.

13. The process of claim 1 further comprising purifying the solid oxidation product wherein the purifying process steps are selected from the group of process steps consisting of washing, separating, drying, solvent contacting, and combinations thereof.

14. The process of claim 1 wherein the oxidizing step further produces a mother liquor.

15. The process of claim 14 further comprising separating the solid oxidation product from the mother liquor, washing the oxidation product, and drying the oxidation product to produce a solid terephthalic acid composition having a 4-carboxybenzaldehyde content of less than 400 ppm-wt.

16. The process of claim 15 wherein the solid terephthalic acid composition has a 4-carboxybenzaldehyde content of less than 100 ppm-wt.

* * * * *